United States Patent [19]

Suzuki et al.

[11] Patent Number: 4,907,876
[45] Date of Patent: Mar. 13, 1990

[54] EXAMINATION APPARATUS FOR MEASURING OXYGENATION IN BODY ORGANS

[75] Inventors: Susumu Suzuki; Sumio Yagi; Naotoshi Hakamata; Takeo Ozaki, all of Shizuoka, Japan

[73] Assignee: Hamamatsu Photonics Kabushiki Kaisha, Shizuoka, Japan

[21] Appl. No.: 188,957

[22] Filed: May 2, 1988

[30] Foreign Application Priority Data

May 8, 1987 [JP] Japan .................. 62-110465
May 8, 1987 [JP] Japan .................. 62-110472

[51] Int. Cl.⁴ .................. G01N 33/49; A61B 5/00
[52] U.S. Cl. .................. 356/41; 128/633
[58] Field of Search .................. 128/633; 250/207; 356/41, 325

[56] References Cited

U.S. PATENT DOCUMENTS

| | | | |
|---|---|---|---|
| 3,794,425 | 2/1974 | Smith et al. | 356/51 |
| 3,905,706 | 9/1975 | Pearl et al. | 250/207 X |
| 4,158,505 | 6/1979 | Mathisen et al. | 356/325 X |
| 4,223,680 | 9/1980 | Jobsis | 128/633 |
| 4,281,645 | 4/1983 | Jobsis | 128/633 |
| 4,321,930 | 3/1982 | Jobsis et al. | 128/633 |
| 4,380,240 | 4/1983 | Jobsis et al. | 128/633 |
| 4,510,938 | 4/1985 | Jobsis et al. | 128/633 |

FOREIGN PATENT DOCUMENTS 0075171 3/1983 European Pat. Off.
0102816 3/1984 European Pat. Off.
2075668A 11/1981 United Kingdom.
2143319A 2/1985 United Kingdom.

OTHER PUBLICATIONS

Tamura, M. et al., "Measurement of Living Body Near Infrared Light Spectrophotometry", Near-Infrared Tissue Spectroscopy, vol. 23, No. 4, pp. 377-385, 1986 (In Japanese).
Wyatt, J. S. et al., "Quantification of Cerebral Oxygenation and Haemodynamics in Sick Newborn Infants by Near Infrared Spectrophotometry", The Lancet, pp. 1063-1066, Nov. 8, 1986.
Komarov, L. I. et al, "Recording Variable Radiation by Discrete-Photon Counting Method", Journal of Applied Spectroscopy, vol. 18, No. 3, pp. 349-353, Jan. 1975.
Hosu, K. K. et al., "Optimum Wavelength Selection System for Component Analyzer", Patent Abstracts of Japan, vol. 11, No. 79, Mar. 11, 1987.

Primary Examiner—Vincent P. McGraw
Attorney, Agent, or Firm—Finnegan, Henderson, Farabow, Garrett and Dunner

[57] ABSTRACT

An examination apparatus which measures the oxygenation in objects with near infrared light transmission spectrophotometry and that automatically adjusts a transmission light quantity to a magnitude suitable for detection by a photomultiplier tube. The examination apparatus comprises a ring-like ND filter whose transmission factor varies along its circumference, a filter driver for automatically setting a transmission factor of a filter, and a light source control device for automatically controlling output powers of light sources.

7 Claims, 6 Drawing Sheets

EXAMINATION APPARATUS FOR MEASURING OXYGENATION IN BODY ORGANS

BACKGROUND OF THE INVENTION

The present invention relates to the apparatus for measuring the oxygen quantity in objects such as the cerebral tissues of a human body or an animal. The invention especially relates to the apparatus for measuring the oxygenation of hemoglobin in blood and of cytochrome in cells by detecting those through electromagnetic waves.

In general, in diagnosing the function of a body organ such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive or that the new-born infant will die is high. Even if the new-born infant lives, however, serious problems in body organs may remain as sequela. The insufficiency of oxygen affects every body organ, but especially causes damage in the cerebral tissues.

To examine the oxygen quantity in body organs readily and at the early stage of illness, an examination apparatus disclosed in U.S. Pat. No. 4,281,645 patented on Aug. 4, 1981 has been developed. In this kind of examination apparatus, the variation of oxygen quantity in body organs, especially in the brain, is measured through the absorption spectrum of near infrared light. The absorption is caused by the hemoglobin which is an oxygen-carrying medium in blood and the cytochrome a, $a_3$ which performs oxydation-reduction reaction in cells. As shown in FIG. 1(a), the absorption spectra of near infrared light (700 to 1300 nm), $\alpha_{HbO2}$ and $\alpha_{Hb}$ by oxygenated hemoglobin (HbO$_2$) and disoxygenated hemoglobin (Hb), respectively, are different from each other. And as shown in FIG. 1(b), the absorption spectra of $\alpha_{CyO2}$ and $\alpha_{Cy}$ by oxidized cytochrome a, $a_3$ (CyO$_2$) and reduced cytochrome a, $a_3$ (Cy), respectively, are different from each other. This examination apparatus utilizes the above-described absorption spectra of near infrared light. Four near infrared light rays with different wavelengths, $\lambda_1$, $\lambda_2$, $\lambda_3$ and $\lambda_4$ (e.g. 775 nm, 800 nm, 825 nm and 850 nm) are applied to one side of the patient's head with a time-sharing method and the transmission light rays from the opposite side of the head are in turn detected. By processing these four detected light rays with the prescribed calculation program the density variations of oxygenated hemoglobin (HbO$_2$), disoxygenated hemoglobin (Hb), oxidized cytochrome a, $a_3$ (CyO$_2$) and reduced cytochrome a, $a_3$ (Cy) are calculated. these parameters, in turn, determine the variation of cerebral oxygen quantity.

FIG. 2 shows a system outline of the above-described conventional examination apparatus 45. The conventional examination apparatus 45 includes; light sources such as laser diodes LD1 to LD4 which emit four near infrared light rays with different wavelengths of $\lambda_1$, $\lambda_2$, $\lambda_3$ and $\lambda_4$, respectively; a light source control device 55 which controls output timing of the light sources LD1 to LD4; optical fibers 50-1 to 50-4 which introduces near infrared light rays emitted by the light sources LD1 to LD4 to a patient's head 40; an illumination-side fixture 51 which bundles and holds end portions of the optical fibers 50-1 to 50-4; a detection-side fixture 52 which is fitted to the prescribed position of the opposite side of the patient's head 40; an optical fiber 53 which is held by the detection-side fixture 52 and introduces transmitted near infrared light from the patient's head 40; a transmission light detection device 54 which measures transmission quantity of near infrared light by counting photons of near infrared light introduced by the optical fiber 53; and a computer system 56 which controls the total examination apparatus and determines the variation of oxygen quantity in cerebral tissues being based on the transmission quantity of near infrared light.

The computer system 56 is equipped with a processor 62, a memory 63, output devices 64 such as a display and a printer, and an input device 65 such as a keyboard, and these devices are connected to each other by a system bus 66. The light source control device 55 and the transmission light detection device 54 are connected to the system bus 66 as external I/O's.

The light source control device 55 receives instructions from the computer system 56 and drives the light sources LD1 to LD4 by respective driving signals ACT1 to ACT4 as shown in FIGS. 3(a) to 3(d). As shown in FIG. 3 one measuring period $M_k$ (k=1, 2, ... .) consists of N cycles of CY1 to CYn. At a phase $\phi n1$ in an arbitrary cycle CYn, no light source of LD1 to LD4 is driven and therefore the patient's head 40 is not illuminated by the near infrared light from the light sources LD1 to LD4. At the phase $\phi n2$ the light source LD1 is driven and the near infrared light with the wavelength of, for example, 775 nm is emitted from it. In the same manner, at the phase $\phi n3$ the light source LD2 is driven and the near infrared light with the wavelength of, for example, 800 nm is emitted from it; at the phase $\phi n4$ the light source LD3 is driven and the near infrared light with the wavelength of, for example, 825 nm is emitted from it; and at the phase $\phi n5$ the light source LD4 is driven and the near infrared light with the wavelength of, for example 850 nm is emitted from it. In this manner the light source control device 55 drives the light sources LD1 and LD4 sequentially with a time-sharing method.

Referring again to FIG. 5, the transmission light detection device 54 is equipped with a filter 57 which adjusts the quantity of near infrared light outputted to lenses 70 and 71 from the optical fiber 53; a photomultiplier tube 58 which converts the light from the filter 57 into pulse current and outputs it; an amplifier 59 which amplifies the pulse current from the photomultiplier tube 58; an amplitude discriminator 60 which eliminates the pulse current from the amplifier 59 whose amplitude is smaller than the prescribed threshold value; a multichannel photon-counter 61 which detects photon frequency in every channel; a detection controller 67 which controls detection periods of the multi-channel photon-counter 61; and a temperature controller 68 which controls the temperature of a cooler 69 containing the photomultiplier tube 58.

To use the above-described examination apparatus, the illumination-side fixture and the detection-side fixture are firmly fitted to the prescribed positions of the patient's head 40 by using tape or the like. Once fitted, the light sources LD1 to LD4 are driven by the light source control device 55 as shown in FIGS. 3(a) to 3(d), respectively, so that the four near infrared light rays with different wavelengths are emitted from the light sources LD1 to LD4 sequentially with the time-sharing method and the light rays are introduced by the optical fibers 50-1 to 50-4 to the patient's head 40. As bones and soft tissues in the patient's head 40 are transparent to the near infrared light, the near infrared light is partially absorbed by hemoglobin in blood and cytochrome a, $a_3$ in cells and outputted to the optical fiber 53. The optical fiber 53 introduces the light to the transmission light detection device 54. At the phase $\phi n1$ no light source of LD1 to LD4 is driven, and therefore, the transmission light detection device 54 detects dark light.

The photomultiplier tube 58 in the transmission light detection device 54 is used with a photon-counting device that has high sensitivity and operates at high response speed. The output pulse current from the photomultiplier tube 58 is sent to the amplitude discriminator 60 through the amplifier 59. The amplitude discriminator 60 eliminates the noise component whose amplitude is smaller than the prescribed amplitude threshold and sends only the signal pulse to the multi-channel photon-counter 61. The multi-channel photon-counter 61 detects photons only in the periods $T_o$. The periods $T_o$ are synchronized with the driving signals ACT1 to ACT4 for the respective light sources LD1 to LD4 as shown in FIGS. 3(a) to 3(d) by a control signal CTL as shown in FIG. 3(e). The control signal CTL is generated by the detection controller 67. The multi-channel photon-counter then counts detected photons of every light with each wavelength sent from the optical fiber 53. The transmission data of every near infrared light with each wavelength are obtained through the above-described procedure.

That is, as shown in FIGS. 3(a) to 3(e), at the phase $\phi n1$ in the cycle CYn of light source control device 55 no light source of LD1 to LD4 is driven, therefore the dark light data d are counted by the transmission light detection device 54. At the phases $\phi n2$ to $\phi n5$ the light sources LD1 to LD4 are sequentially driven with the time-sharing method and the transmission light detection device 54 sequentially counts the transmission data $t\lambda_1$, $\lambda_2$, $t\lambda_3$ and $t\lambda_4$ of the respective near infrared light rays with different wavelengths $\lambda_1$, $\lambda_2$, $\lambda_3$ and $\lambda_4$.

The counting of the dark light data d and the transmission data $t\lambda_1$, $t\lambda_2$, $t\lambda_3$ and $t\lambda_4$ which is sequentially performed in the cycle CYn, is continued N times from CY1 to CYn. That is, one measuring period $M_k$ (k=1, 2, ...) includes N cycles. A concrete example is as follows; if one cycle is 200 $\mu$sec and N is 10000, the measuring period $M_k$ becomes 2 sec. At the time of finishing of one measuring period $M_k$, the counting result of the dark light data $$D\left( = \sum_{n=1}^{N} d/CYn \right)$$

and the counting results of the transmission data $$T_{\lambda 1}, T_{\lambda 2}, T_{\lambda 3} \text{ and } T_{\lambda 4} \left( = \sum_{n=1}^{N} t\lambda_j/CYn \right)$$

are transferred to the computer system 56 and stored in the memory 63.

The processor 62 performs the subtraction of the dark light component by using the combination of the transmission data and the dark data $(T_{\lambda 1}, T_{\lambda 2}, T_{\lambda 3}, T_{\lambda 4}, D)M_k$ being stored in the memory 63 after one measuring period $M_k$ and the combination of those $(T_{\lambda 1}, T_{\lambda 2}, T_{\lambda 3}, T_{\lambda 4}, D)M_o$ at the start of measuring, and calculates the variation rates of the transmission light $\Delta T_{\lambda 1}$, $\Delta T_{\lambda 2}$, $\Delta T_{\lambda 3}$ and $\Delta T_{\lambda 4}$. That is, the variation rates of the transmission light $\Delta T_{\lambda 1}$, $\Delta T_{\lambda 2}$, $\Delta T_{\lambda 3}$ and $\Delta T_{\lambda 4}$ are calculated as:

$$\Delta T_{\lambda j} = \log\left[(T_{\lambda j} - D)_{Mk}/(T_{\lambda j} - D)_{Mo}\right] (j=1 \text{ to } 4). \tag{1}$$

The use of logarithm in the above calculation of $\Delta T_{\lambda j}$ is to express the variation as an optical density.

Using the above-calculated variation rates of the transmission light $\Delta T_{\lambda 1}$, $\Delta T_{\lambda 2}$, $\Delta T_{\lambda 3}$ and $\Delta T_{\lambda 4}$, density variations of oxygenated hemoglobin (HbO$_2$), disoxygenated hemoglobin (Hb), oxidized cytochrome a, $a_3$ (CyO$_2$) and reduced cytochrome a, $a_3$ which are expressed as $\Delta X_{HbO2}$, $\Delta X_{Hb}$, $\Delta X_{CyO2}$ and $\Delta X_{Cy}$, respectively, can be determined. That is, each of density variations of $\Delta X_{HbO2}$, $\Delta X_{Hb}$, $\Delta X_{CyO2}$ and $\Delta X_{Cy}$ is calculated as:

$$\Delta X_i = \sum_{j=1}^{4} (\alpha_{ij})^{-1} \Delta T_{\lambda j}/l \tag{2}$$

where $\alpha_{ij}$ is an absorption coefficient of each component i (HbO$_2$, Hb, CyO$_2$, Cy) for each Wavelength $\lambda_j$ ($\lambda_1$, $\lambda_2$, $\lambda_3$, $\lambda_4$) and is predetermined from FIGS. 1(a) and 1(b), and l is the length of the patient's head 40 along the travelling direction of the near infrared light.

As the above-detected density variation components, $\Delta X_{HbO2}$, $\Delta X_{Hb}$, $\Delta X_{CyO2}$ and $\Delta X_{Cy}$, reflect the variation of oxygen quantity in the brain, the variation of oxygen quantity in the brain can be determined by outputting these detected results from the output device 64. The diagnosis is thus made based on these results.

The transmission quantity of the near infrared light greatly varies in the order of $10^4$ to $10^5$ with the size of the head 40, that is, the length l of the head 40 in the traveling direction of the near infrared light. Even if it is assumed that the size of the head 40 is kept constant being independent of the patient, as the output powers of the light sources (laser diodes) LD1 to LD4 vary in the order of $10^1$ to $10^2$ with their wavelengths of $\lambda_1$, $\lambda_2$, $\lambda_3$ and $\lambda_4$ (775 nm, 800 nm, 825 nm and 850 nm, respectively), the transmission quantities also vary sequentially in the order of $10^1$ to $10^2$.

On the other hand, it is desired that the light quantity which is made incident on the photomultiplier tube 58 in the transmission light detection device 54 during the measurement should be kept almost constant being independent of the length l of the head 40 and the variation of the output powers of the light sources LD1 to LD4 with the wavelengths, because the dynamic range of the photomultiplier tube 58 is approximately in the order of $10^2$.

Therefore, in the conventional examination apparatus 45, a variable light-attenuating ND (Neutral-Density) filter is employed as the filter 57, whose transmission factor can be manually adjusted. When the examination of one object person is started, the transmission factor of the filter 57 and each of the output powers of the light sources LD1 to LD4 are manually adjusted so that the incident light quantity on the photomultiplier tube 58, that is, the transmission light quantity becomes an optimum value.

As described above, the conventional examination apparatus has a problem that because of the manual adjustments of the filter 57 and the output powers of the light sources LD1 to LD4 it is difficult to adjust the transmission light quantity to the optimum value quickly and accurately. In addition, when the near infrared light transmitted from the head 40 is too intense the transmission quantity information incident on the photomultiplier tube 58 is cut off through attenuating the transmission quantity by the filter 57, which prevents the improvement of the measurement accuracy.

Another problem is that as the transmission factor of the filter 57 is kept constant after adjustment at the start of measurement, the variation of the transmission factor during the measurement caused by the position change of the filter 57 can not be restored. This also prevents the accurate measurement.

SUMMARY OF THE INVENTION

Accordingly, an object of the present invention is to provide an examination apparatus which can adjust the transmission light quantity quickly and accurately so that the light quantity becomes suitable for the detection and can also obtain the accurate measurement result.

An examination apparatus according to the first aspect of the invention comprises: plural light sources for emitting respective electromagnetic waves with different wavelengths; a light source control means for controlling the plural light sources so that the electromagnetic waves emitted from the light sources are sequentially made incident on a measuring object; and a transmission light detection means for detecting electromagnetic waves transmitted from the measuring object; and is characterized in that: the transmission light detection means comprises a filter for attenuating electromagnetic waves transmitted from the measuring object, and a filter driving means for varying a transmission factor of the filter; the light source control means and the filter driving means control output powers of the plural light sources and the transmission factor of the filter, respectively, so that transmission quantities of the electromagnetic waves become suitable for the detection. Previous to an actual measurement of the oxygenation the transmission factor of the filter and the output powers of the plural light sources are controlled so that the transmission quantities of the electromagnetic waves from the measuring object become suitable values.

An examination apparatus according to the second aspect of the invention comprises: a light source means for sequentially emitting electromagnetic waves with different wavelengths; and a transmission light detection means for sequentially detecting transmission quantities of the electromagnetic waves transmitted from a measuring object; and is characterized in that: the transmission light detection means detects each transmission quantity of electromagnetic wave with its wavelength with a detection mode suitable for the magnitude of each transmission quantity. For example, when the transmission quantity is small the transmission quantity is detected with a "photon-counting mode", and when the transmission quantity is large that is detected with an "analog detection mode".

Other and further objects, features and advantages of the invention will appear more fully from the following description taken in connection with the accompanying drawings.

DETAILED DESCRIPTION OF THE PREFERRED EMBODIMENTS

The first aspect of the present invention will be described in the following.

Figure 1A:
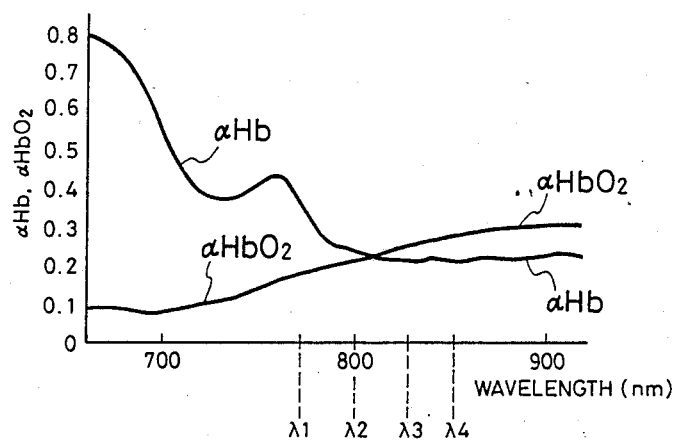
FIGS. 1(a) and 1(b) are graphs showing absorption spectra of hemoglobin and cytochrome, respectively.
Figure 1B:
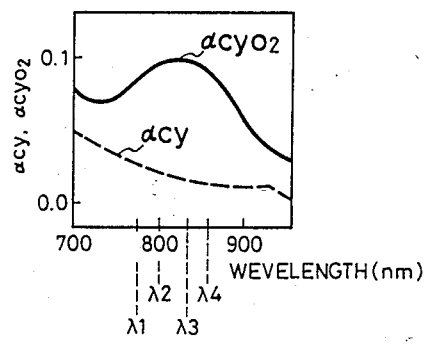
Figure 2:
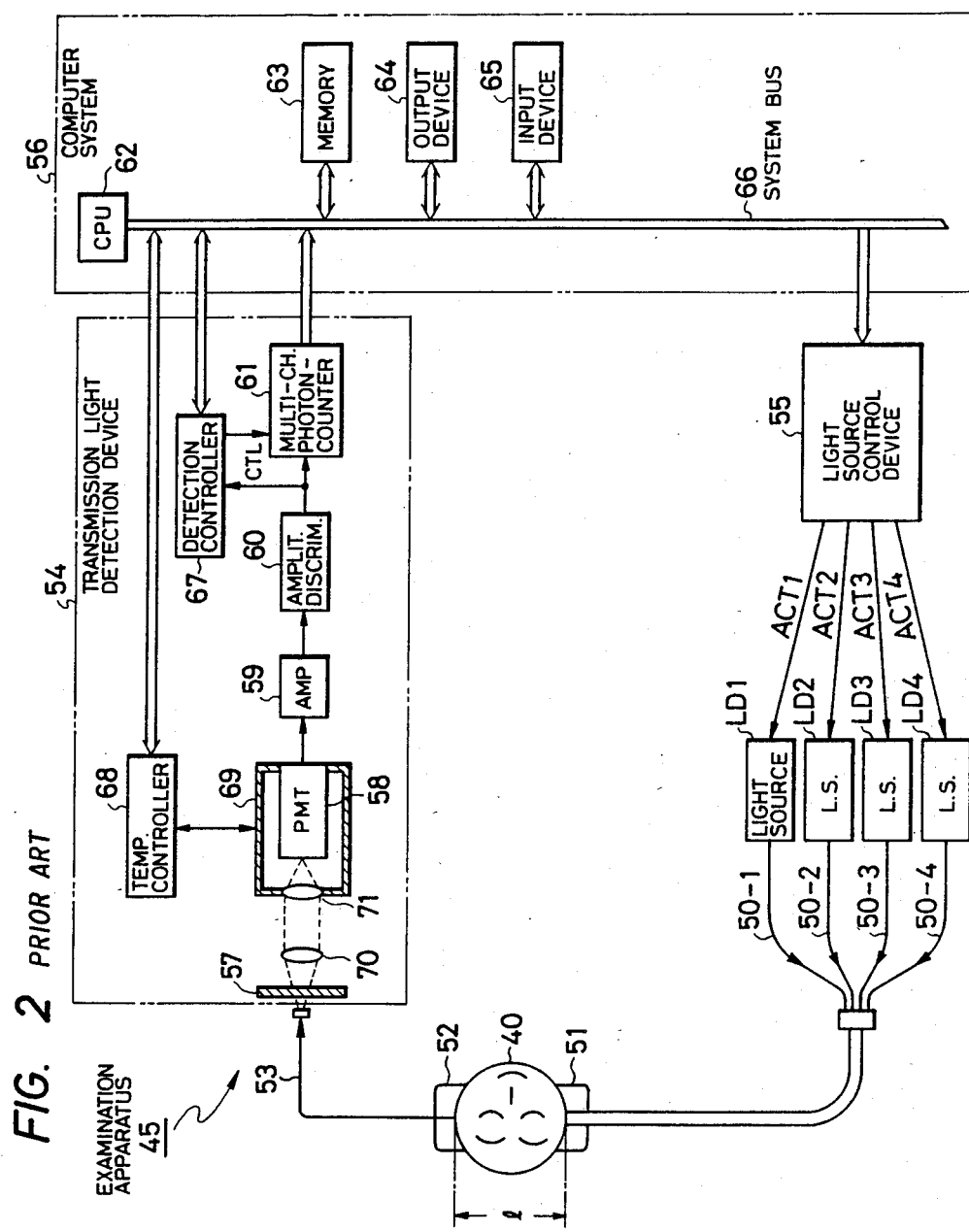
FIG. 2 is a block diagram showing a system constitution of a conventional examination apparatus.
Figure 3:
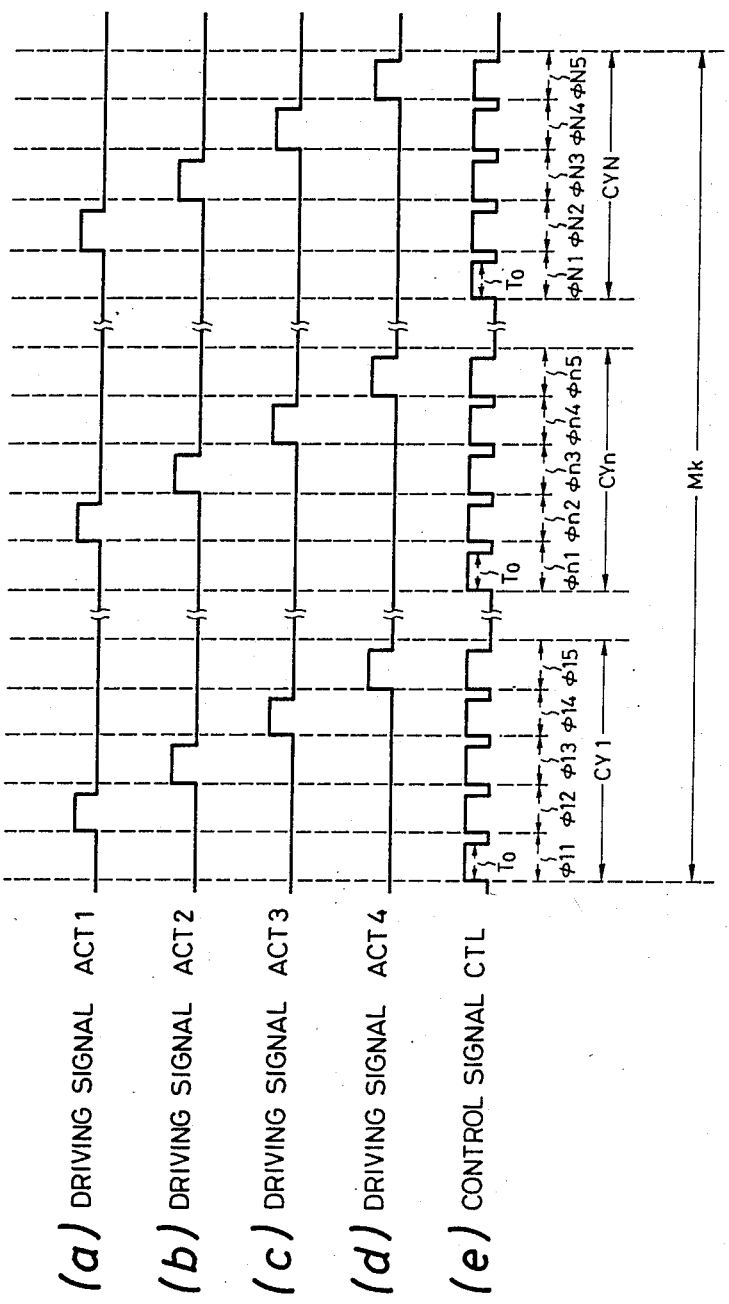
FIGS. 3(a) to 3(e) are time-charts of driving signals ACT1 to ACT4 and a control signal CTL, respectively.
Figure 4:
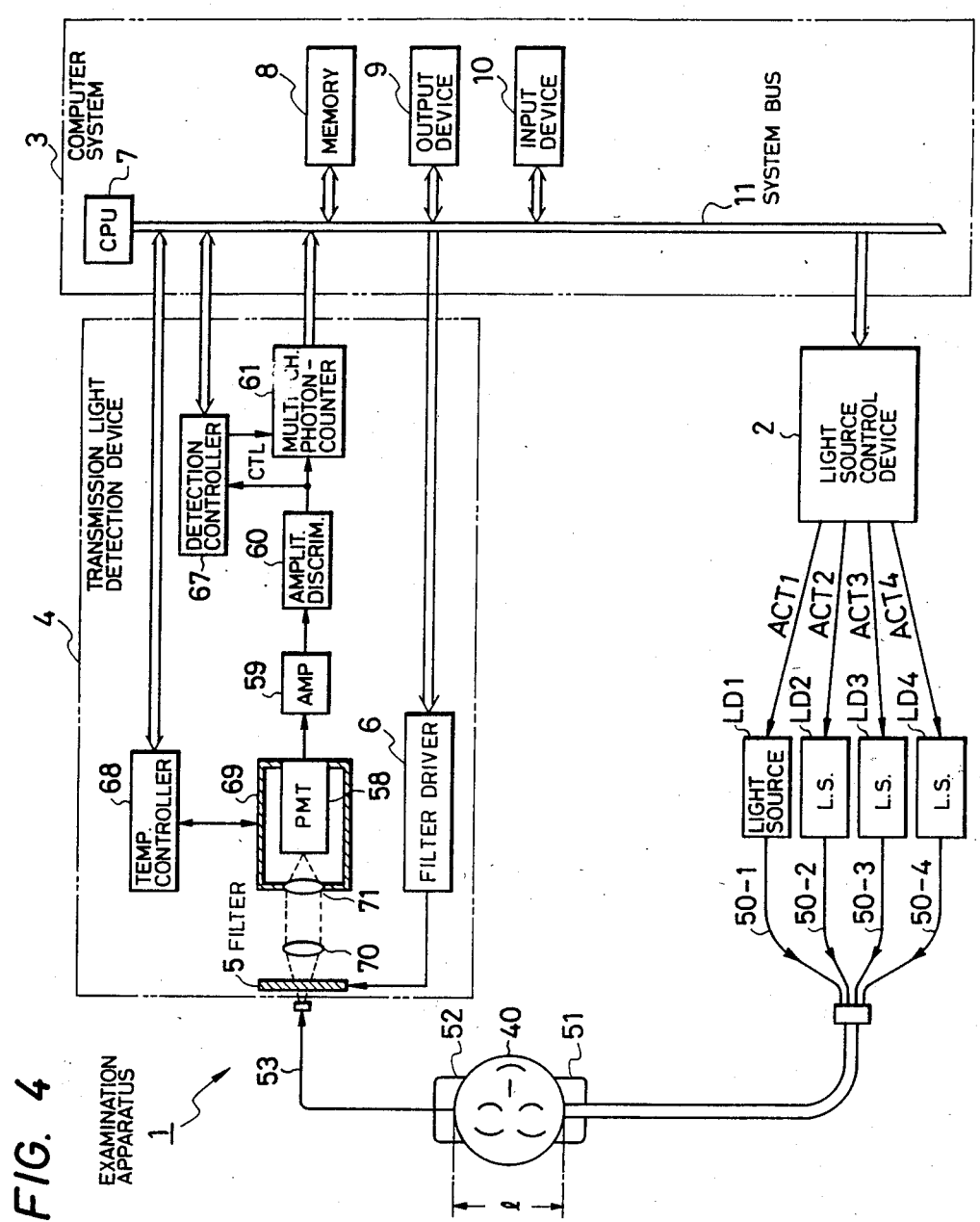
FIG. 4 is a block diagram showing a system constitution of an examination apparatus according to the first aspect of the present invention.

FIG. 4 is a block diagram showing an system constitution of an examination apparatus according to the first aspect of the invention. The same blocks, parts or signals in FIG. 4 as those in FIG. 2 are designated by the same reference numerals or numbers as those in FIG. 2, and the explanation of those will be omitted.

A light control device 2 of an examination apparatus 1 in FIG. 4 automatically controls output powers of light sources LD1 to LD4 according to an instruction from a computer system 3 so that transmission quantities of near infrared light rays to be detected by a transmission light detection device 4 become optimum not depending on wavelengths $\lambda_1$, $\lambda_2$, $\lambda_3$ and $\lambda_4$.

A filter driver 6 in the transmission light detection device 4 controls a transmission factor of a filter 5 within its variable range of transmission factor according to an instruction from the computer system 3 so that the light quantity incident on a photomultiplier tube 58 does not vary even if sizes of heads 40, that is, lengths l of heads 40 vary from one object person to another. The computer system 3, in the same manner as in the conventional computer system 56, has a constitution that a processor 7, a memory 8, an output device 9 and input device 10 are connected to a system bus 11. Furthermore, the computer system controls the light source control device 2 so that the light source control device 2 automatically controls the output powers of the light sources LD1 to LD4, and also controls the filter driver 6 so that the filter driver 6 automatically adjusts the transmission factor of the filter 5.

The operation of the above-described examination apparatus will be described in the following. In the period $M_o$ of the beginning of measurement, at phases $\phi n2$ to $\phi n5$ in one cycle CYn the light sources LD1 to LD4 are sequentially driven in a time sharing method and transmission light quantity data $t_{\lambda 1}$, $t_{\lambda 2}$, $t_{\lambda 3}$ and $t_{\lambda 4}$ of the near infrared light rays with respective four different wavelengths of $\lambda_1$, $\lambda_2$, $\lambda_3$ and $\lambda_4$ are sequentially counted in the transmission light detection device 4. In the same procedure, the transmission light quantity data $t_{\lambda 1}$, $t_{\lambda 2}$, $t_{\lambda 3}$ and $t_{\lambda 4}$ which are sequentially counted in a cycle CYn are continuously counted over N cycles (CY1 to CYN) in the period $M_o$ of the beginning of measurement. After the measurement of the Nth cycle CYN, the counted results $(T_{\lambda 1}, T_{\lambda 2}, T_{\lambda 3}, T_{\lambda 4})_{Mo}$ are transferred to the computer system 3 and stored in the memory 8. The processor 7 judges whether each of the transmission quantity data $(T_{\lambda 1}, T_{\lambda 2}, T_{\lambda 3}, T_{\lambda 4})_{Mo}$ is optimum, or not. Furthermore, the processor 7 judges whether the transmission quantity data $T_{\lambda 1}$ to $T_{\lambda 4}$ are different from one another (with wavelength), or not.

If the computer system 3 judges that the transmission quantity data $T_{\lambda 1}$ to $T_{\lambda 4}$ are not optimum, it makes the filter driver 6 operate so as to change the transmission factor of the filter 5 by an appropriate amount and also changes the output powers of the light sources LD1 to LD4 by an appropriate amount. Furthermore, if the transmission quantity data $T_{\lambda 1}$ to $T_{\lambda 4}$ are different from one another, the computer system 3 changes the transmission factor of the filter 5 and the output powers of the light sources LD1 to LD4 with wavelengths so as to eliminate the variation in the transmission quantity data. The optimum transmission factors and the optimum output powers of the light sources LD1 to LD4 at every wavelength which have been obtained in the above procedure, are stored in the memory 8.

The optimum transmission factors and the output powers of the light sources LD1 to LD4 at every wavelength which were stored in the memory 8 in the period $M_o$ of the beginning of measurement, are used in the actual measurement of the oxygenation to automatically control the transmission factor of the filter 5 and the output powers of the light sources LD1 to LD4. That is, in a subsequent measuring period $M_k$ ($k=1, 2, \ldots$), when the transmission quantity data are measured at phases $\phi n2$ to $\phi n5$ in a cycle CYn the processor 7 changes the transmission factor of the filter 5 and the output powers of the light sources LD1 to LD4 on the basis of the optimum transmission factor and the optimum output powers at every phase which are stored in the memory 8. In this procedure the cerebral oxygenation can be measured with sequentially changing the transmission factor of the filter 5 and the output powers of the light sources LD1 to LD4 automatically so as to make the transmission quantities optimum.

Figure 5:
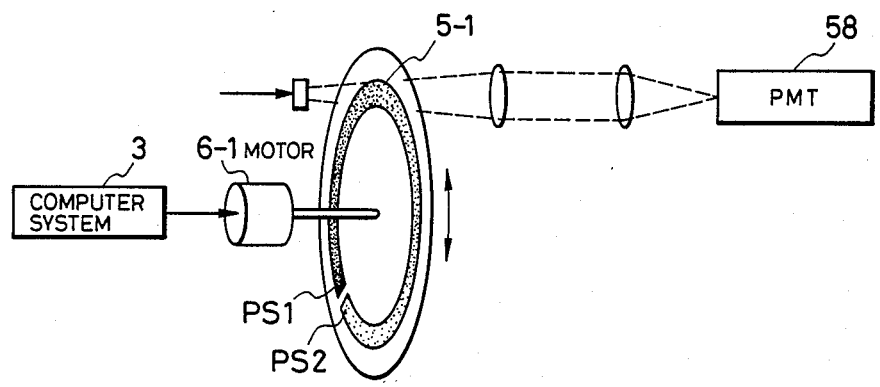
FIG. 5 is a drawing illustrating a constitution of a filter and a filter driver shown in FIG. 4.

FIG. 5 illustrates an embodiment of the filter 5 and the filter driver 6 shown in FIG. 4. A filter 5-1 in FIG. 5 is a ring-like ND (Neutral-Density) filter whose transmission factor gradually varies along its circumference. The filter 5-1 is driven in the rotational direction by a motor 6-1. If a portion PS1 of the filter 5-1 with a minimum transmission factor is located in the optical axis, the light quantity of the near infrared light which is to be made incident on the photomultiplier tube 58 is attenuated most. On the other hand, if a portion PS2 with a maximum transmission factor is located in the optical axis, the light quantity of the near infrared light which is to be made incident on the photomultiplier tube 58 is attenuated least. The motor 6-1 is for example a pulse motor and controlled by the computer system 3.

With the constitutions of the filter 5-1 and the motor 6-1 as shown in FIG. 5, even if the length l, of the head 40 varies with the object persons, the computer system 3 can locate the portion of the filter 5-1 with the appropriate transmission factor in the optical axis by rotating the filter 5-1 by the appropriate amount by the motor 6-1 in the manner as described above.

As the transmission factor can be automatically determined with the simple mechanism without a manual operation as described in the foregoing, the manipulation of the examination apparatus become much easier.

However, as the filter 5-1 is mechanically rotated by the motor 6-1 in the above embodiment, it may be expected in the long use that the accuracy in positioning the appropriate portion of the filter 5-1 in the optical axis, and accuracy in other parts may be deteriorated and thereby the reliability of the examination data may be decreased. Moreover, as mechanical parts are used, the above embodiment is not suitable to miniaturize the examination apparatus. Further disadvantage is that much electric power is dissipated by the motor 6-1.

Figure 6:
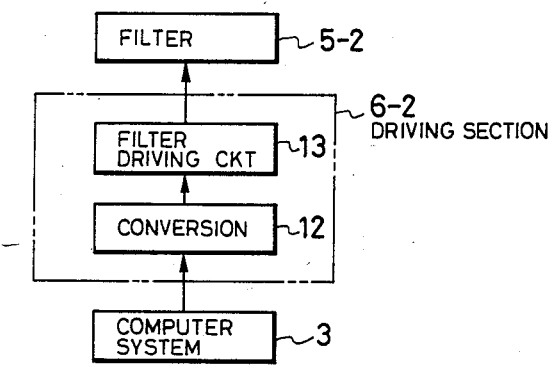
FIG. 6 is a block diagram showing another constitution of a filter and a filter driver shown in FIG. 4.

FIG. 6 shows another embodiment of the filter and the filter driver which can further improve the reliability of the examination apparatus and can miniaturize the examination apparatus.

A filter 5-2 in FIG. 6 consists of a liquid crystal panel. As the light-attenuating factor of a liquid crystal panel varies with an applied voltage, the transmission factor of the filter 5-2 can be made variable by using this characteristics of a liquid crystal panel.

The filter 5-2 consisting of the liquid crystal panel is connected to the driving section 6-2 which applies a driving voltage to the filter 5-2. The driving section 6-2 comprises a conversion part 12 which converts a control signal from the computer system 3 into a transmission factor, and a driving circuit 13 which applies the driving voltage corresponding to the transmission factor converted by the conversion part 12 to the filter 5-2.

The conversion part 12 converts the control signal sent from the computer system 3 into the transmission factor which is for example proportional to the amplitude of the control signal. In this case, as the driving voltage applied to the filter 5-2 consisting of the liquid crystal panel is proportional to the amplitude of the control signal from the computer system 3, the light-attenuating factor of the filter 5-2 can be linearly varied by varying the amplitude of the control signal by the computer system 3. If the conversion part 12 converts the control signal from the computer system into the transmission factor non-linearly, the resultant light-attenuating factor of the filter 5-2 varies non-linearly to the variation of the control signal which is determined by the computer system.

As described above, as there is no part which is mechanically controlled when the liquid crystal panel is employed as the filter 5-2, the reliability of the examination apparatus does not decrease even in the long use, the examination apparatus can be miniaturized, and the electric power dissipated in the examination apparatus can be reduced.

The second aspect of the invention will be described in the following.

Figure 7:
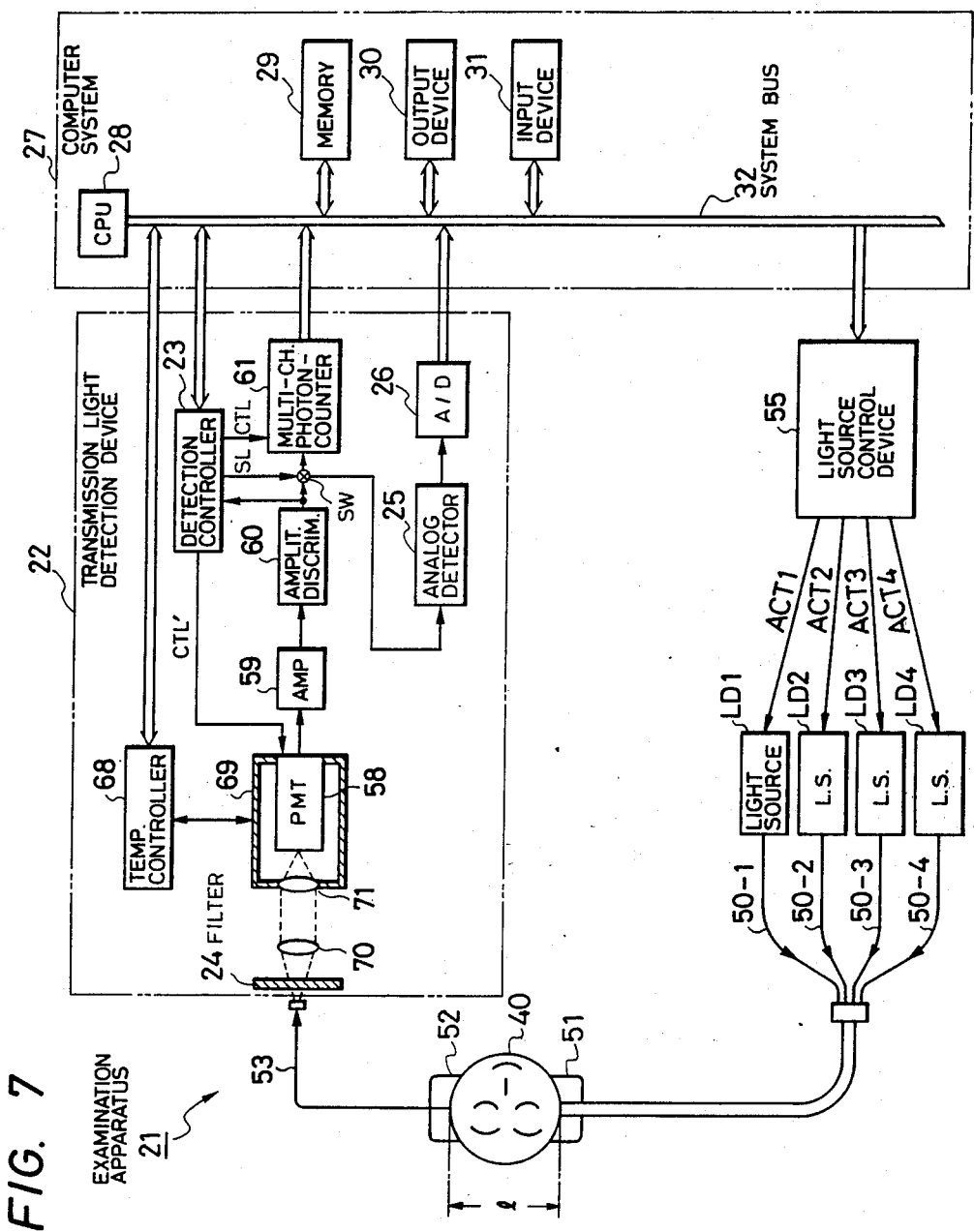
FIG. 7 is a block diagram showing a system constitution of an examination apparatus according to the second aspect of the invention.

FIG. 7 shows a system constitution of an examination apparatus according to the second aspect of the invention. The same blocks, parts or signals in FIG. 7 as those in FIG. 2 are designated by the same reference numerals or numbers as those in FIG. 2 and the description of those will be omitted.

In an examination apparatus 21 in FIG. 7, a transmission light detection device 22 is equipped with a detection controller 23 which controls a detection period of a multi-channel photon-counter 61 and adjusts the gain of a photomultiplier tube 58 by controlling a voltage applied to the photomultiplier tube 58. More specifically, the detection controller 23 controls the detection period of the multi-channel photo-counter 61 according to an instruction from a computer system 22 and also adjusts the voltage applied to the photomultiplier tube 58 according to an amplitude of current which is obtained through photoelectric conversion by the photomultiplier tube 58, amplification by an amplifier 59 and amplitude discrimination by an amplitude discriminator 60. The voltage applied to the photomultiplier tube 58 is adjusted through a control signal CTL'.

In this embodiment, the transmission factor of a filter 24 is set on the basis of the case in which the light quantity of the transmission light is minimum. Therefore, when the light quantity of the transmission light introduced by an optical fiber 53 is small, an prescribed quantity of the transmission light is made incident on the photomultiplier tube 58, a pulse current is outputted from the photomultiplier tube 58, and the detection controller 23 controls the voltage applied to the photomultiplier tube 58 (that is, the gain of the photomultiplier tube) on the basis of the pulse current so that the photomultiplier tube 58 operates with a "photon-counting mode". On the other hand, when the light quantity of the transmission light is large, a large quantity of the transmission light is made incident on the photomultiplier tube 58 and an analog current is outputted from the photomultiplier tube 58. The detection controller 23 controls the gain of the photomultiplier tube 58 on the basis of the analog current so that the photomultiplier tube 58 operates with an "analog detection mode".

The transmission light detection device 22 of the examination apparatus 21 in FIG. 7 is equipped with the multi-channel photon-counter 61 which is the same as the conventional one and counts in a digital method the number of pulse currents (that is, the number of photons) outputted from the photomultiplier tube 58 when the transmission light quantity incident on the photomultiplier tube 58 is small, and also equipped with an analog detector 25 which detects the analog current outputted from the photomultiplier tube 58 when the transmission light quantity incident on the photomultiplier tube 58 is large. The selection of the device for detecting the output current from the photomultiplier tube 58 from the multi-channel photon-counter 61 and the analog detector 25 is made by changing over of switch SW through a selection signal SL. the analog detector 25 has a wide dynamic range and the analog current detected by the analog detector 25 is sent to the computer system 27 after being A/D-converted by an A/D converter 26.

In the computer system 27, a processor 28, a memory 29, an output device 30 and an input device 31 are connected to a system bus 32 in the same manner as in the conventional computer system 56. Furthermore, the computer system 27 has a function to control the detection controller 23 as described above.

In the examination apparatus 21 with the above-described constitution, as the transmission factor of the filter 24 is previously set on the basis of the case with the minimum light quantity of the transmission light introduced by the optical fiber 53, the light quantity of the transmission light incident on the photomultiplier tube 58 greatly varies depending on the size of the head 40 or the variation in the absorption quantity by the head 40 with the wavelength. Therefore, it is necessary before the actual oxygenation measurement to initially test whether the transmission light quantity is small and the photomultiplier tube 58 is operating with the photon-counting mode, or the transmission light quantity is large and the photomultiplier tube 58 is operating with the analog detection mode.

This initial test can be performed in the period $M_o$ of the beginning of the examination. At the phase $\phi n2$ in one cycle CYn in the period $M_o$, the near infrared light with the wavelength of $\lambda_1$ is emitted from the light source LD1 and the transmission light with the wavelength of $\lambda_1$ from the head 40 is made incident on the photomultiplier tube 58 through the filter 24. The output current corresponding to the transmission light quantity is outputted from the photomultiplier tube 58 and sent to the detection controller 23.

In the same manner, at the phases $\phi n3$, $\phi n4$ and $\phi n5$ in one cycle CYn in the period $M_o$ the near infrared light rays with the respective wavelengths of $\lambda_2$, $\lambda_3$ and $\lambda_4$ are sequentially emitted from the respective light sources LD2, LD3 and LD4. And the transmission light rays with the wavelengths of $\lambda_2$, $\lambda_3$ and $\lambda_4$ from the head 40 are sequentially made incident on the photomultiplier tube 58 through the filter 24 in a time-sharing method. The output currents corresponding to the respective transmission light quantities are outputted from the photomultiplier tube 58 and sent to the detection controller 23. In this procedure, on the basis of the output currents at every wavelength outputted over prescribed times of cycles CY1 to CYN in the period $M_o$ of the beginning of the examination, the detection controller 23 judges whether the output currents correspond to the photo-counting mode or the analog detection mode. The result of this judgment is stored in the memory 29 of the computer system 27. The initial setting of the detection modes at every wavelength is completed with the foregoing procedure.

The detection modes initially set for every wavelength of $\lambda_1$ to $\lambda_4$ are used in each of the cycles CY1 to CYN in the measuring period $M_k$ in which the actual oxygenation measurements are performed. That is, at the phase $\phi n2$ in the cycle CYn in the measuring period $M_k$, the detection controller 23 gets the detection mode initially set for the wavelength $\lambda_1$ out of the memory 29, adjusts the gain of the photomultiplier tube 58 through the control signal CTL' according to this detection mode, and changes over the switch SW through the selection signal SL. For example, if the detection mode for the wavelength of $\lambda_1$ stored in the memory 29 is the photon-counting mode, the detection controller adjusts the gain of the photomultiplier tube 58 to the value suitable for the photon-counting mode and changes over the switch SW to the multi-channel photon-counter 61.

At other phases $\phi n3$, $\phi n4$ and $\phi n5$ in the cycle CYn, the detection controller 23 gets the detection modes initially set for the respective wavelengths $\lambda_2$, $\lambda_3$ and $\lambda_4$ out of the memory 29, adjusts the gain of the photomultiplier tube 58 through the control signal CTL' according to these detection modes, and changes over the switch SW through the selection signal SL.

As described in the foregoing, as the transmission light quantity can be measured with the appropriate detection mode corresponding to the transmission light quantity incident on the photomultiplier tube 58, it is not necessary to cut off the information of the transmission quantity even when the transmission quantity is large and thereby the accurate measurement results can be obtained.

Though in the foregoing embodiment the detection modes are initially set in the period $M_o$ of the beginning of the examination, without performing the initial setting of the detection modes the transmission light quantity may be detected with both detection modes regardless of the magnitude of the transmission light quantity by changing over the photon-counting mode and the analog detection mode within one phase with the time-sharing method. In this case, two kinds of the transmission quantity data which are detected with the photon-counting mode and the analog detection mode are stored in the memory 29 at the end of the one measuring period $M_k$. The processor 28 judges which data are appropriate, selects the appropriate data, and outputs the selected data to the output device 30.

Though the foregoing embodiments are described with four light sources of LD1 to LD4, the number of the light sources is not limited to four, but may be two or more than four.

Moreover, though the foregoing embodiments are described with plural light sources, the electromagnetic waves with different wavelengths may be obtained by using only one white light source and filtering the white light emitted from the white light source. The application of the examination apparatus according to the invention is not limited to the medical field, but covers many fields including mere measurements. The measuring object is not limited to body organ, but may be general object such as a piece of flesh. Furthermore, the electromagnetic wave emitted from the light source is not limited to the near infrared light, but may be far infrared light, visible light, or microwave.

What is claimed is:

1. An examination apparatus for measuring the oxygenation in an object with electromagnetic wave transmission spectrophotometry, comprising:
    plural light sources for emitting respective electromagnetic waves with different wavelengths;
    light source control means for controlling said plural light sources so as to sequentially emit said electromagnetic waves;
    an illumination-side fixture for making said electromagnetic waves introduced from said light sources incident on a measuring object;
    a detection-side fixture for detecting electromagnetic waves transmitted from said measuring object and sending said transmitted electromagnetic waves to transmission light detection means;
    said transmission light detection means for detecting said transmitted electromagnetic waves introduced from said detection-side fixture and outputting transmission light data; and
    a computer system for controlling said light source control means and said transmission light detection means, and for receiving said transmission light data from said transmission light detection means and calculating the oxygenation in said measuring object; wherein
    said transmission light detection means includes filter means with a variable transmission factor for attenuating said transmitted electromagnetic waves and filter driving means for setting said transmission factor of said filter means; and
    said light source control means and said filter driving means control output powers of said plural light sources and said transmission factor of said filter means, respectively, so that a light quantity outputted from said filter means become suitable for the detection.

2. An examination apparatus as claimed in claim 1, wherein optimum output powers of said respective light sources and optimum transmission factors for said respective electromagnetic waves with different wavelengths are previously determined at the beginning of the measurement and stored in said computer system, and said light source control mean and said filter driving means control said output powers of said plural light sources and said transmission factor of said filter means on the basis of said optimum output powers and said optimum transmission factors being stored in said computer system, respectively, in the actual oxygenation measurement.

3. An examination apparatus as claimed in claim 1, wherein
    said filter means is a ring-like ND filter whose transmission factor gradually varies along its circumference; and
    said filter driving means is a motor which sets said transmission factor of said ring-like N/D filter by locating an appropriate portion of said ring-like ND filter in the optical axis by rotating said ring-like ND filter according to an instruction from said computer system.

4. An examination apparatus as claimed in claim 1, wherein
    said filter means is a liquid crystal panel whose transmission factor varies with an applied driving voltage; and
    said filter driving means receives a control signal from said computer system, converting said control signal into a transmission factor signal, and applies an appropriate driving voltage corresponding to said transmission factor signal to said liquid crystal panel.

5. An examination apparatus for measuring the oxygenation in an object with the electromagnetic wave transmission spectrophotometry, comprising:
    light source means for emitting electromagnetic waves with respective different wavelengths;
    light source control means for controlling said light source means so as to sequentially emit said electromagnetic waves;
    an illumination-side fixture for making said electromagnetic waves introduced from said light source means incident on a measuring object;
    a detection-side fixture for detecting electromagnetic waves transmitted from said measuring object and sending said transmitted electromagnetic waves to transmission light detection means;
    said transmission light detection means for detecting said transmitted electromagnetic waves introduced from said detection-side fixture with a photomultiplier tube and outputting transmission light data, said transmission light detection means further includes a photon-counter and an analog detector for detecting an output current from said photomultiplier tube, said output current from said photomultiplier tube is detected by said photon-counter with a photon-counting mode when a transmission light quantity incident on said photomultiplier tube is small, and is detected by said analog detector with an analog detection mode when said transmission light quantity is large, and said transmission light detection means further includes a detection controller for receiving said output current from said photomultiplier tube and for selecting the detection mode from said photon-counting mode and said analog detection mode and controlling a voltage applied to said photomultiplier tube according to said received output current; and
    a computer system for controlling said light source control means and said transmission light detection means, and for receiving said transmission light data from said transmission light detection means and calculating the oxygenation in said measuring object; wherein
    said transmission light detection means detects each of said transmitted electromagnetic waves with a detection mode suitable for intensity of each of said transmitted electromagnetic waves.

6. An examination apparatus as claimed in claim 5, wherein appropriate detection modes for said respective electromagnetic waves with different wavelengths are previously determined at the beginning of the measurement and stored in said computer system, and said computer system controls said transmission light detection means on the basis of said stored appropriate detection modes so that said detection mode is appropriately selected in the actual oxygenation measurement.

7. An examination apparatus for measuring the oxygenation in an object with electromagnetic wave transmission spectrophotometry, comprising:
  light source means for emitting electromagnetic wave with respective different wavelengths;
  light source control means for controlling said light source means so as to sequentially emit said electromagnetic waves;
  an illumination-side fixture for making said electromagnetic waves introduced from said light source means incident on a measuring object;
  a detection-side fixture for detecting electromagnetic waves transmitted from said measuring object and sending said transmitted electromagnetic waves to transmission light detection means;
  said transmission light detection means for detecting said transmitted electromagnetic waves introduced from said detection-side fixture with a photomultiplier tube and outputting transmission light data, said transmission light detection means further includes a photon-counter and an analog detector for detecting an output current from said photomultiplier tube, and said output current from said photomultiplier tube is detected by both of said photo-counter and said analog detector with a photon-counting mode and an analog detection mode, respectively, for each of said electromagnetic waves with different wavelengths, and a computer system selects appropriate transmission light data from transmission light data obtained with said photo-counting mode and said analog detection mode; and
  said computer system for controlling said light source control means and said transmission light detection means, and for receiving said transmission light data from said transmission light detection means and calculating the oxygenation in said measuring object; wherein
  said transmission light detection means detects each of said transmitted electromagnetic waves with a detection mode suitable for intensity of each of said transmitted electromagnetic wave.

* * * * *